US 6,683,118 B1

(12) United States Patent
Hofs

(10) Patent No.: US 6,683,118 B1
(45) Date of Patent: Jan. 27, 2004

(54) METHOD FOR HYDROFORMYLATING OLEFINICALLY UNSATURATED COMPOUNDS

(75) Inventor: Wolfgang Hofs, Oberhausen (DE)

(73) Assignee: Celanese Chemicals Europe GmbH (DE)

( * ) Notice: Subject to any disclaimer, the term of this patent is extended or adjusted under 35 U.S.C. 154(b) by 8 days.

(21) Appl. No.: 10/129,249

(22) PCT Filed: Nov. 4, 2000

(86) PCT No.: PCT/EP00/10881
§ 371 (c)(1),
(2), (4) Date: Apr. 30, 2002

(87) PCT Pub. No.: WO01/36361
PCT Pub. Date: May 25, 2001

(30) Foreign Application Priority Data

Nov. 13, 1999 (DE) .......................................... 199 54 665

(51) Int. Cl.⁷ .......................... C07C 27/00; C07C 27/06; C07C 45/00

(52) U.S. Cl. ........................................ 518/701; 568/454
(58) Field of Search ........................... 518/701; 568/454

(56) References Cited

U.S. PATENT DOCUMENTS

| 4,523,036 A | * | 6/1985 | Cornils et al. | 568/454 |
| 5,773,666 A | * | 6/1998 | Omatsu et al. | 568/484 |
| 5,808,168 A | * | 9/1998 | Bahrmann et al. | 568/484 |
| 6,555,716 B2 | * | 4/2003 | Protzmann et al. | 568/451 |

FOREIGN PATENT DOCUMENTS

DE   2627354   12/1976

* cited by examiner

Primary Examiner—Mukund J. Shah
Assistant Examiner—Zachary C. Tucker
(74) Attorney, Agent, or Firm—Muserlian, Lucas and Mercanti

(57) ABSTRACT

According to the inventive method, the hydroformylation of the olefinically unsaturated compounds is carried out in the presence of an aqueous, water-soluble catalyst solution containing rhodium complex compounds, in a reaction column.

16 Claims, 2 Drawing Sheets

METHOD FOR HYDROFORMYLATING OLEFINICALLY UNSATURATED COMPOUNDS

This application is a 371 of PCT/EP00/10881 filed Nov. 4, 2000.

The invention relates to an improved process for the hydroformylation of olefinically unsaturated compounds in the presence of an aqueous catalyst solution comprising water-soluble rhodium complexes by use of a reaction column as reactor.

The reaction of compounds containing olefinic double bonds with carbon monoxide and hydrogen is the customary industrial method of preparing aldehydes (oxo process).

The process is not restricted to the use of olefinic hydrocarbons, but can be extended to starting materials which not only have a double bond but also bear functional groups, predominantly groups which remain, unchanged under the reaction conditions.

The classical oxo process employs cobalt as catalyst. Its effectiveness is based on the formation of cobalt carbonyl compounds by action of hydrogen and carbon monoxide at pressures above 20 MPa and temperatures of about 120° C. and more on metallic cobalt or cobalt compounds.

In the last 30 years, cobalt has increasingly been replaced by rhodium as catalyst. The platinum metal is used as a complex which comprises, preferably, phosphenes as ligands in addition to carbon monoxide. The use of rhodium as catalyst allows the process to be carried out at lower pressures and, in addition, higher yields are achieved and the unbranched products which are more valuable for further processing are preferentially formed if straight-chain terminal olefins are used as starting materials.

A further refinement of the oxo process comprises the transition from catalysts which are homogeneously dissolved in the reaction medium, i.e. in the starting material and in the reaction product, to aqueous catalyst solutions which are present as a separate phase in addition to that formed by the starting material and reaction product. This variant of the reaction is described, for example, in DE B-26 27 354. Its particular advantage is that the reaction product and the catalyst can readily be separated under mild conditions without use of thermal process steps, so that losses which occur as a result of further reactions of the aldehydes formed are avoided. Furthermore, very high yields are achieved and, when using unbranched terminal olefins, the aldehydes obtained are very predominantly n-aldehydes.

In practice, the oxo process using an aqueous catalyst phase is usually carried out in stirred reactors which have initially been charged with a solution of the catalyst system in water. Olefinically unsaturated compounds and synthesis gas are introduced into the reaction vessel and reacted with one another with intimate mixing. The reaction product leaves the reactor together with aqueous catalyst solution, unreacted starting materials (synthesis gas, olefin) and hydrogenation products of the olefinically unsaturated compounds via an immersed tube. The gas phase, essentially synthesis gas, olefin and saturated hydrocarbon formed from the olefin, is separated from the liquid products in a separation vessel and recirculated to the reactor. Part of the circulating gas is freed of the condensable reaction products in a condenser and is discharged into the waste gas system.

The liquid separated off in the separation vessel is passed to a phase separator. Here, the crude organic reaction product separates from the aqueous catalyst phase. While the organic reaction product is conveyed via a pump to a stripping column, a further pump conveys the aqueous catalyst phase back to the reactor with the heat of the exothermic reaction being removed in a heat exchanger and used to generate process steam. Water can be fed to the reactor together with the cooled catalyst solution to compensate water losses which occur via the waste gas and via the oxo product. The crude oxo product introduced into the stripping column is conveyed in countercurrent to part of the synthesis gas which in this way becomes laden with the olefin dissolved in the crude product. The preheated synthesis gas/olefin mixture is fed to the reactor. A further substream of synthesis gas is preheated in a heat exchanger using process heat. The fresh olefin is also preheated and vaporized in a heat exchanger by means of waste heat from the aldehyde distillation before it enters the reactor, while the crude oxo product from the stripping column is passed directly without cooling to the distillation. Finally, a buffer vessel for temporary storage of product is provided in case of a malfunction in the plant.

In an industrially particularly advantageous embodiment of a production plant for carrying out the oxo process, synthesis gas and olefin are introduced via double roses which serve as predistributors into the reactor in which the aqueous catalyst solution is present. The fine dispersion of the reactants in the reaction mixture is achieved by means of a sparging stirrer. To remove the heat of reaction, the reactor is provided with a cooling matrix. The liquid and gaseous components ascend through a guide tube in the reactor and separate at its upper end. The gas is either recirculated into the reactor or discharged from the reaction system as offgas. The aqueous catalyst solution separates from the crude, organic product. The crude product is introduced into a stripping column, freed of dissolved olefins by means of the synthesis gas passed through the stripping column in countercurrent and finely fractionated into its components in a column. The heat required for the distillation is obtained directly via the cooling matrix. For this purpose, the liquid aldehyde from the bottom of the column is introduced via a phase separator into the cooling matrix in which it vaporizes and it is then conveyed in vapor form via the phase separator back into the column.

The above-described apparatus for carrying out the oxo process using an aqueous catalyst phase has given excellent service in industrial practice. However, there is interest in further optimizing the process. This is an object of the present invention. Specifically, the invention has the object of improving the economics by changing the way in which the process is carried out and/or by simplifying the apparatus employed in the process. Further objects are to increase the conversion and the yield of desired product and to improve safety.

The invention provides a process for the hydroformylation of olefinically unsaturated compounds in a heterogeneous reaction system using a catalyst consisting of an aqueous solution comprising complexes of rhodium with water-soluble organic phosphorus(III) compounds as ligands and, if desired, excess water-soluble organic phosphorus(III) compounds, at pressures of from 0.4 to 10 MPa and temperatures of from 50 to 180° C. According to the present invention, the reaction of the reactants is carried out in a reaction column.

Apart from carrying out the reaction between olefinic compound and synthesis gas in a heterogeneous reaction system using an aqueous catalyst phase, it is an essential feature of the invention that the reaction is carried out in a reaction column as reactor.

The differences between the novel process and the processes customary hitherto which have a stirred tank as central apparatus of the reaction plant are conspicuous. Apart from further changes, the mixing of the reactants and the catalyst solution without use of a stirrer and the absence of a separate stripping apparatus for recovering the olefin dissolved in the product are of particular significance.

For the purposes of the present invention, the term reaction columns refers to the apparatuses used, in particular, for distillation, rectification and extraction in chemical engineering. As hydroformylation reactors, they are provided with feed openings for the reactants and the catalyst solution and with devices for taking off product, catalyst solution and offgas. As reaction columns, it is possible to use the various types of column which are widely used in industrial practice, in particular tray columns and columns with ordered packing or random packing elements. In these, the catalyst solution is fed in at the top of the column, advantageously onto the uppermost tray of the column. Below the top of the column, preferably in the upper region (i.e. in the upper half) of the column, the olefinic compound is fed into the reactor. Catalyst solution, olefin and reaction product, which travel downward in the interior of the column, flow in countercurrent to the ascending synthesis gas introduced at the bottom of the column. Reaction product and catalyst solution are taken off in the lower part (the lower half) of the reactor, while the gaseous components leave the column in its upper region.

The reactants and catalyst solution do not have to be introduced into the reactor at one feed point each. It is thus not necessary for the total amount of olefin to be introduced entirely at one point and in the upper region and the total amount of synthesis gas to flow into the reaction space only at the bottom of the reaction column. Rather, the reactants can be introduced at different points along the column. The number of feed points can be up to the number of separation stages of the column. Equipping the reactor with a plurality of feed lines for the individual participants in the reaction allows it to be matched individually to the requirements of the respective reaction, e.g. with regard to the reactivity of the olefin used, the desired reaction rate, the completeness of the conversion and the desired composition of the reaction product. Merely by way of example, the reactivity of the olefin will be examined in more detail. In the case of olefins which react quickly, a larger amount of olefin will be able to be fed to the reactor than in the case of relatively unreactive olefins, so that the reactive unsaturated hydrocarbons are introduced into the reactor via not only one feed line but via a plurality of feed lines. This opportunity of varying the streams also allows the same reactor to be used for reacting various starting materials. The introduction of catalyst solution at various points along the reactor will be restricted to special cases, e.g. to maintain the required catalyst concentration in the case of increased catalyst consumption caused by impurities in the starting materials or else to control the temperature by removing heat of reaction from the reactor. Below the top of the reactor, it is possible to feed the catalyst solution into the column either separately from the olefin or together with the olefin.

Use of a reaction column instead of a stirred tank as reactor is also advantageous because a plurality of separation stages (e.g. column trays) are connected in series in the column. The series arrangement of a plurality of separation stages in the column has the effect of converting the characteristics of a stirred tank into the characteristics of a cascade of stirred tanks. Olefin and synthesis gas react with one another in the presence of the catalyst solution until the respective chemical and physical equilibrium is established. For this reason, the conversion in the reaction column is higher than in a stirred tank. Reaction columns having from 5 to 120 separation stages, in particular from 15 to 40 separation stages, have been found to be useful in the process of the invention.

A critical factor in the choice of the reaction column which is suitable in a particular case is its load range. This term refers to the uniform hydrodynamic loading of the column cross section due to ascending gas/mass stream and the downflowing liquid/mass stream. Each reaction column has a particular load range which depends on the type of column internals and the properties of the feed mixture and within which uniform flow loading and thus heat and mass transport are ensured.

The hydroformylation reaction is strongly exothermic. The heat evolved in the reaction can be used either internally in the reaction for preheating the reactants and for distillation of the reaction product and/or externally for generating steam. The thermal energy is advantageously removed via the reaction product and the circulated catalyst solution, although heat recovery is not restricted to these embodiments.

The synthesis gas rising through the reaction column flows, as stated above, in countercurrent to the reaction product. The gaseous phase permeates the liquid stream and in the process extracts unreacted olefin dissolved in the reaction product and transports it into the reaction zone. The olefin conversion is significantly improved in this way, without a specific extraction unit having to be installed in the hydroformylation plant.

As catalysts, use is made of water-soluble rhodium complexes containing water-soluble phosphorus(III) compounds as ligands. Examples of watersoluble phosphorus (III) compounds which form complexes with rhodium are triarylphosphines, trialkylphosphines and arylated or alkylated diphosphines whose organic radicals contain sulfonic acid groups or carboxyl groups. Their preparation and use is known, for example, from DE-B-26 27 354, EP 0 103 810 B1, EP 0 163 234 B1 and EP 0 571 819 A1. Further groups of suitable compounds are sulfonated or carboxylated organic phosphites and heterocyclic compounds of trivalent phosphorus.

The conditions under which the reaction occurs can be varied within wide limits and adapted to individual circumstances. They depend, inter alia, on the starting material, on the catalyst system chosen and on the desired degree of conversion. The hydroformylation of the starting materials is usually carried out at temperatures of from 50 to 180° C. Preference is given to temperatures of from 80 to 140° C, in particular from 100 to 130° C. The total pressure is in a range from 0.4 to 10 MPa, preferably from 1 to 6 MPa and in particular from 1.5 to 5 MPa. The molar ratio of hydrogen to carbon monoxide is usually in the range from 1:10 to 10:1; mixtures comprising hydrogen and carbon monoxide in a molar ratio of from 3:1 to 1:3, in particular 1:1, are preferred.

The rhodium concentration is from 20 to 1000 ppm by weight, preferably from 50 to 500 ppm by weight and in particular from 100 to 300 ppm by weight, in each case based on the aqueous catalyst solution. Although it is possible to use the stochiometric rhodium-phosphorus complex as catalyst, the reaction is preferably carried out in the presence of excess phosphorus ligand, i.e. ligand which has not undergone complex formation with rhodium. Preference is given to using from 3 to 200 mol of phosphorus in the form of a water-soluble organic phosphorus compound per mol of rhodium. Molar ratios of rhodium to phosphorus in the range from 1:50 to 1:100 have been found to be particularly useful. The rhodium-phosphorus complex used as catalyst does not have to have a uniform composition, but can be, for example, a mixture of rhodium complexes which differ in the type of phosphorus ligands present. Likewise, the phosphorus ligand present in the aqueous catalyst solution can be composed of a mixture of different water-soluble organic phosphorus compounds. The catalyst is usually formed from the components rhodium or rhodium compound, organic phosphorus compound and synthesis gas under the conditions of the hydroformylation reaction. However, it can also be introduced into the reaction stage as a preformed catalyst, i.e. a separately prepared catalyst. It has been found to be advantageous to circulate the catalyst and to make up for any catalyst losses which occur by introduction of fresh catalyst.

To increase the conversion per unit time of olefinically unsaturated compounds which are only sparingly soluble in the aqueous catalyst solution, it may be advisable to add a phase transfer reagent (solubilizer) to this solution. This alters the physical properties of the interfaces between the two liquid phases and thus aids transition of the organic reactants into the aqueous catalyst phase. Solubilizing action is displayed by compounds whose hydrophilic groups are ionic (anionic or cationic) or nonionic. Examples of anionically active compounds are, inter alia, the sodium, potassium and ammonium salts of carboxylic acids, preferably those having from 8 to 20 carbon atoms. Cationic solubilizers include tetraalkylammonium and N-alkylpyrridinium salts. Nonionic phase transfer reagents are, for example, alkyl and alkylphenyl polyethylene glycols and trialkylamine oxides.

The reactants olefin and synthesis gas can be preheated before introduction into the reactor. The liquid phase leaves the reaction column in the lower part, preferably at the bottom of the column, and goes via a heat exchanger into a phase separator. Here, it separates into the organic reaction product and the aqueous catalyst solution. The offgas taken from the reactor in the upper part, in particular at the top of the column, consists essentially of carbon monoxide and hydrogen. It may further comprise reaction product, saturated compounds formed by hydrogenation of the olefinic compounds and water. Olefinic starting material is present in the offgas particularly when, for example for reasons of process economics, the reaction has not been carried out to complete conversion of the unsaturated compound. The olefin can be recovered from the offgas by known methods, e.g. by condensation, or reacted in a second reaction stage to convert it into hydroformylation product. The reaction product present in the offgas is also separated off and returned to the reaction column or passed directly to the distillation stage.

The process of the invention can be applied to olefinically unsaturated compounds of any structure. Accordingly, both olefins having an internal double bond and olefins-having terminal double bonds and likewise straight-chain or branched olefins are suitable as starting material. Furthermore, the olefins can also be substituted by functional groups, in particular groups which are not changed during the course of the reaction.

Multiply olefinically unsaturated compounds are also possible as starting materials. The process has been found to be particularly useful in the hydroformylation of olefinically unsaturated hydrocarbons having from 3 to 12 carbon atoms in the molecule, preferably propylene and the isomeric butenes.

Possible embodiments of the process of the invention are shown schematically by way of example in the accompanying drawings.

BRIEF DESCRIPTION OF THE DRAWINGS

In the process outlined in FIG. 1, synthesis gas is fed into a reaction column 1 at the bottom of the column via a line 2 and olefin is fed in at feed points 4, 5 and 6 along the length of the reactor via a line 3. The catalyst solution is pumped via a line 7 into the top of the column and onto the uppermost separation stage of the column. Downward-flowing olefin reacts in the reactor with ascending synthesis gas in the presence of the catalyst to form aldehyde until equilibrium is established. Olefin dissolved in the product is stripped from the liquid phase by the upward-flowing synthesis gas stream and is likewise converted into aldehyde. The crude aldehyde which has been freed of olefin is taken off together with the catalyst solution in the lower part of the reaction column and is passed directly via a line 8 to a heat exchanger 9. The recovered heat can be used, for example, for the generation of stream and/or for the distillation of reaction product. The heat exchanger is followed by a separator 10 in which organic product and aqueous catalyst solution are separated. The catalyst phase is pumped via a heat exchanger 11, where the remaining heat in it is removed, to the top of the reaction column 1, if appropriate after addition of supplementary amounts of water or catalyst solution from containers 12 and 13. Offgas is taken from the reaction system via line 14. It comprises predominantly carbon monoxide and hydrogen and small amounts of, inter alia, unreacted olefin and reaction product. Olefin and product are not discarded but instead can, like carbon monoxide and hydrogen, be utilized, for example in the process itself. It is also possible for the gas mixture to be reacted in an after-reactor with the olefin recovered from the offgas so as to convert both of them into further, desired product.

The process variant shown in FIG. 2 differs from the process of FIG. 1 in that the offgas leaving the reactor 1 via line 14 is cooled in a heat exchanger 15. A two-phase system consisting of gaseous and liquid phase is formed. Both phases are separated in a separator 16 and the gaseous phase is removed from the system while the liquid phase is returned to the reaction column 1 via line 17. The plant components denoted by the reference numerals 2 to 13 correspond, (as do the reaction column 1 and the offgas line 14) to those of FIG. 1.

Figure 1:
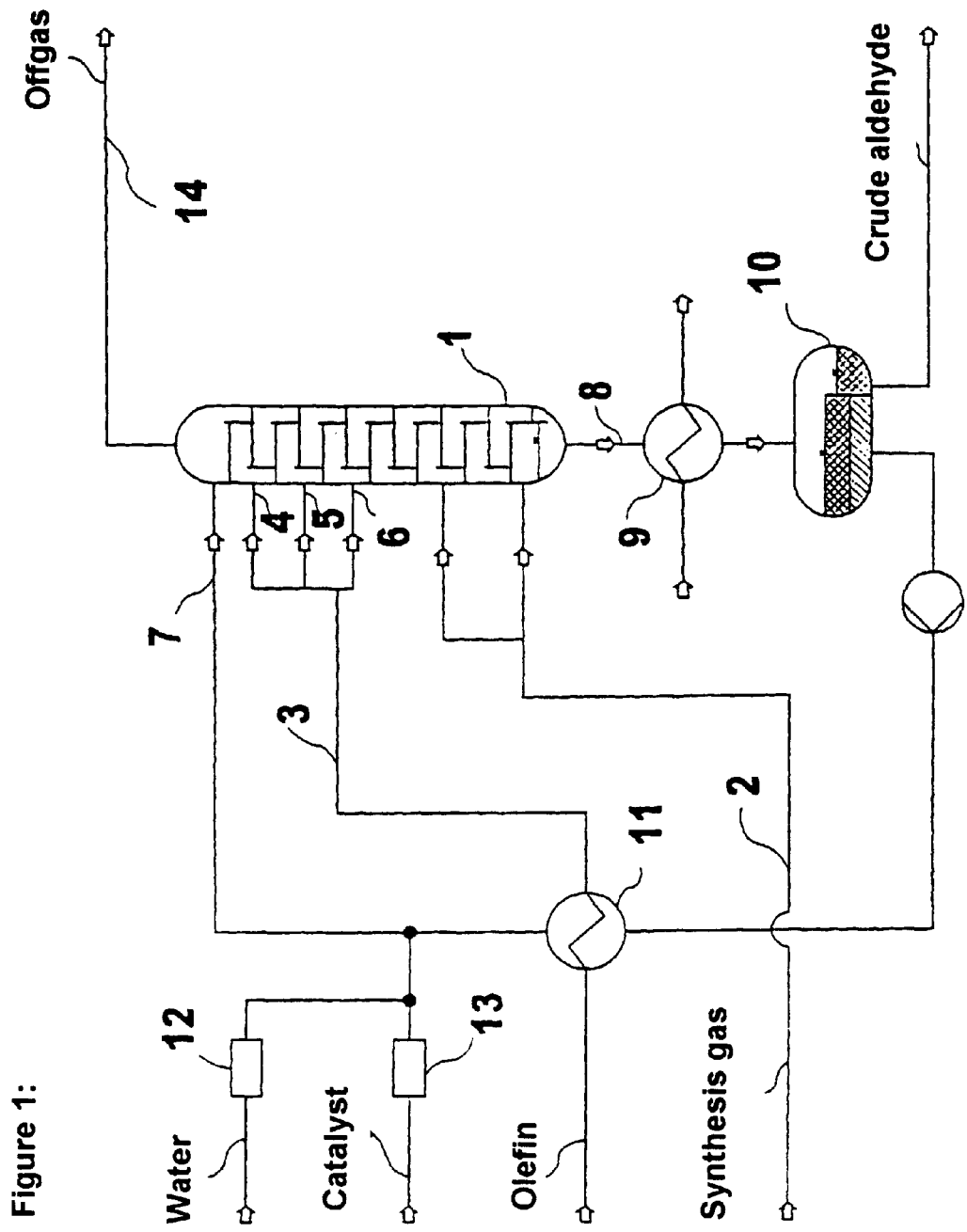
Figure 2:
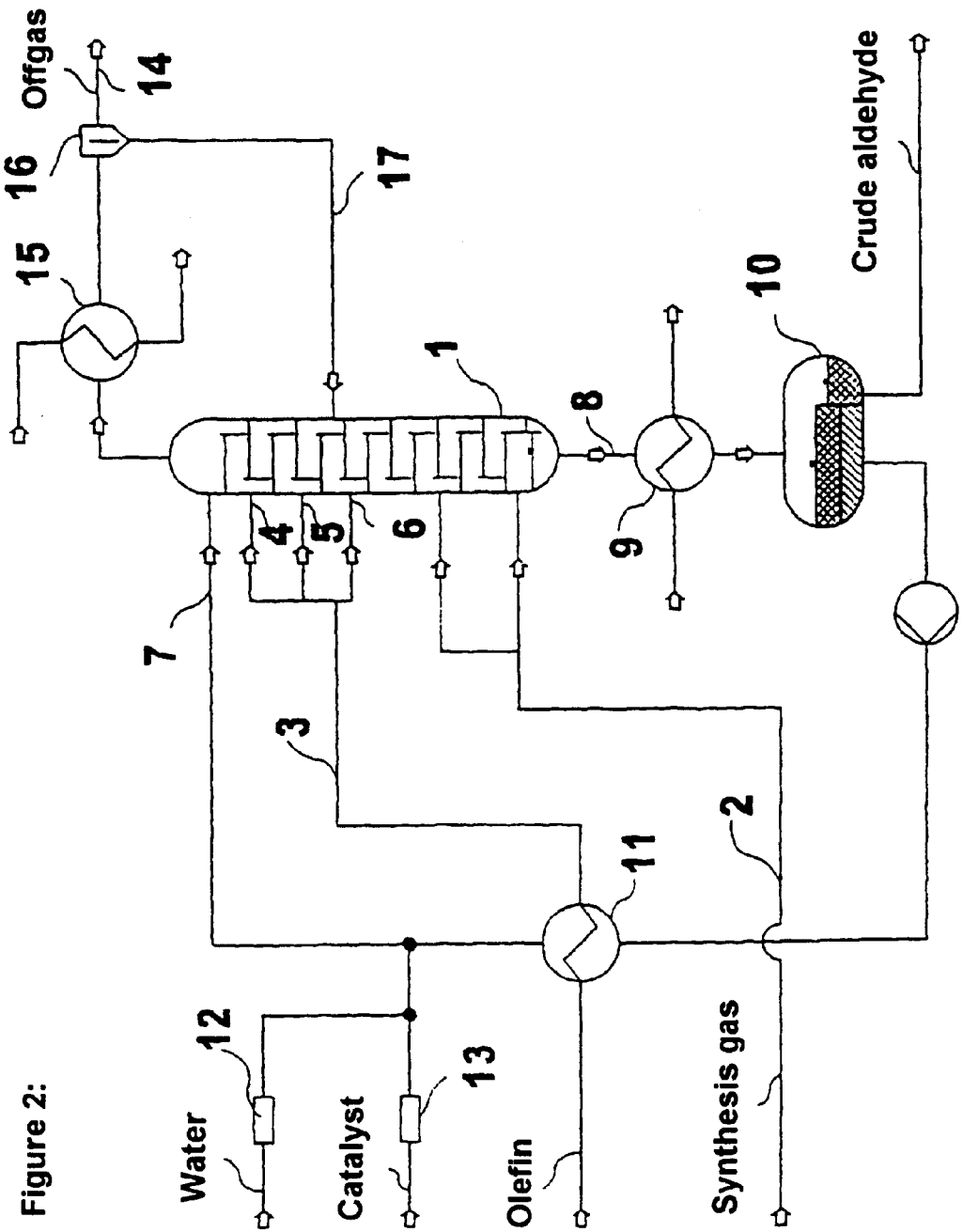

What is claimed is:

1. A process for the hydroformylation of olefinically unsaturated compounds in a heterogeneous reaction system using a catalyst of an aqueous solution comprising complexes of rhodium with water-soluble organic phosphorus (III) compounds as ligands and, optionally excess water-soluble organic phosphorus(III) compounds, at pressures of from 0.4 to 10 MPa and temperatures of from 50 to 180° C., wherein the reaction of the reactants is carried out in a reaction column selected from the group consisting of a tray column, a column with ordered packing and a column with random packing elements.

2. The process of claim 1 wherein the reaction column is provided with feed openings for the reactants and the catalyst solution and with devices for removing product, catalyst solution and offgas.

3. The process of claim 1 wherein the reaction column has from 5 to 120 separation stages.

4. The process of claim 1 wherein the reactants, namely olefinically unsaturated compounds and synthesis gas, and the catalyst solution are fed into the reaction column at separate feed points.

5. The process of claim 1 wherein the olefinically unsaturated compound is introduced in the upper region of the reaction column at one feed point or at a plurality of feed points.

6. The process of claim 1 wherein the synthesis gas is introduced in the lower region of the reaction column at one feed point or at a plurality of feed points.

7. The process of claim 1 wherein the catalyst solution is introduced in the upper region of the reaction column onto the uppermost separation stage of the reaction column.

8. The process of claim 1 wherein the reactants, namely olefinically unsaturated compound and synthesis gas, and the catalyst solution are each introduced at a plurality of feed points arranged along the reaction column.

9. The process of claim 1 wherein olefinically unsaturated compound and catalyst are introduced together below the top of the column or at one or more feed points along the reaction column.

10. The process of claim 1 wherein the reactants are preheated before being introduced into the reaction column.

11. The process of claim 10 wherein preheating is carried out using heat evolved in the process.

12. The process of claim 1 wherein heat of reaction is removed by an auxiliary medium.

13. The process of claim 1 wherein offgas is separated into a gaseous phase and a liquid phase and the liquid phase is returned to the reaction column.

14. The process of claim 12 wherein the auxiliary medium is water or steam.

15. The process of claim 3 wherein the column has 15 to 40 separation stages.

16. The process of claim 6 wherein the synthesis gas is introduced at the bottom of the reaction column.

* * * * *